US006687389B2

(12) United States Patent
McCartney et al.

(10) Patent No.: US 6,687,389 B2
(45) Date of Patent: *Feb. 3, 2004

(54) IMAGING APPARATUS

(75) Inventors: David John McCartney, Ipswich (GB); Christopher Henry Seal, Ipswich (GB)

(73) Assignee: British Telecommunications Public Limited Company, London (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/180,760

(22) PCT Filed: Oct. 23, 1998

(86) PCT No.: PCT/GB98/03177

§ 371 (c)(1),
(2), (4) Date: Nov. 13, 1998

(87) PCT Pub. No.: WO99/21479

PCT Pub. Date: May 6, 1999

(65) Prior Publication Data
US 2002/0164054 A1 Nov. 7, 2002

(30) Foreign Application Priority Data

Oct. 24, 1997 (EP) .............................................. 97308526

(51) Int. Cl.[7] ................................................. G06K 9/00
(52) U.S. Cl. ....................... 382/118; 382/117; 382/190; 382/255; 351/220; 359/534; 359/631; 348/346
(58) Field of Search ................................ 382/117, 190; 357/205, 206, 207, 208, 211, 221, 200–247; 348/156, 150, 346; 713/186; 235/308; 359/631, 534, 632

(56) References Cited

U.S. PATENT DOCUMENTS

| 4,109,237 A | 8/1978 | Hill | 382/117 |
| 4,256,384 A | 3/1981 | Kani et al. | 351/206 |
| 4,266,861 A | 5/1981 | Sawa | 351/206 |

(List continued on next page.)

FOREIGN PATENT DOCUMENTS

| EP | 0061832 A2 | 10/1982 |
| EP | 0534477 A1 | 9/1992 |
| FR | 2461481 | 2/1981 |

(List continued on next page.)

OTHER PUBLICATIONS

Japanese Giant Spends US $25.8M on Iris Scanning Technology, Biometric Technology Today, vol. 3, No. 6, Oct. 1995.
Cope, The Corneal Polarisation Cross, J. Opt. Soc. of America, vol. 68, No. 8, pp 1139–1140, 1978.
Robbins, Biological Perspectives on Human Pigmentation, pp. 74–75, 1991.

(List continued on next page.)

Primary Examiner—Jayanti K. Patel
(74) Attorney, Agent, or Firm—Nixon & Vanderhye PC

(57) ABSTRACT

An imaging apparatus suitable for capturing a image of one or more of a user's facial features is disclosed. The apparatus includes a spherical cold mirror which presents a concave surface to the user and is disposed between the user and the camera. The user is able to conclude that he is close enough to the camera for successful image capture when the reflection he sees in the mirror is the right way up. In a preferred embodiment, markings are provided on the front surface of the mirror to aid the user in placing his eye within a predetermined range of distances from the camera. The imaging apparatus is suitable for use in iris recognition apparatuses and provides a relatively inexpensive alternative to known apparatuses.

10 Claims, 6 Drawing Sheets

U.S. PATENT DOCUMENTS

| | | | |
|---|---|---|---|
| 4,394,074 A | | 7/1983 | McMahon et al. ............ 351/206 |
| 4,533,222 A | | 8/1985 | Ishikawa ..................... 351/206 |
| 4,620,318 A | | 10/1986 | Hill ............................. 382/117 |
| 4,641,349 A | | 2/1987 | Flom et al. .................. 382/117 |
| 4,755,043 A | | 7/1988 | Carter ......................... 351/205 |
| 4,786,142 A | | 11/1988 | Karecki ....................... 359/894 |
| 4,795,224 A | * | 1/1989 | Goto ........................... 359/211 |
| 4,821,118 A | | 4/1989 | Lafreniere .................. 348/156 |
| 4,834,528 A | | 5/1989 | Howland et al. ........... 351/211 |
| 4,993,068 A | | 2/1991 | Piosenka et al. ............ 713/186 |
| 5,118,179 A | | 6/1992 | Sano et al. .................. 351/206 |
| 5,214,454 A | | 5/1993 | Sano ........................... 351/206 |
| 5,291,330 A | * | 3/1994 | Daniels ....................... 359/478 |
| 5,291,560 A | | 3/1994 | Daugman .................... 382/117 |
| 5,357,369 A | * | 10/1994 | Pilling et al. ................ 359/462 |
| 5,359,669 A | * | 10/1994 | Shanley et al. ............. 382/117 |
| 5,433,197 A | | 7/1995 | Stark ........................... 606/319 |
| 5,485,241 A | | 1/1996 | Irie et al. ...................... 396/57 |
| 5,572,596 A | | 11/1996 | Wildes et al. ............... 382/117 |
| 5,573,006 A | * | 11/1996 | Shimotani et al. .......... 340/575 |
| 5,576,796 A | | 11/1996 | Akashi ......................... 396/51 |
| 5,639,151 A | * | 6/1997 | McNelley et al. ............ 353/98 |
| 5,808,589 A | * | 9/1998 | Fergason ........................ 345/8 |
| 5,953,114 A | * | 9/1999 | Spink et al. ................. 351/212 |
| 6,095,651 A | * | 8/2000 | Williams et al. ............ 351/246 |
| 6,309,069 B1 | * | 10/2001 | Seal et al. ................... 351/221 |

FOREIGN PATENT DOCUMENTS

| | | | |
|---|---|---|---|
| FR | | 2516778 | 5/1983 |
| FR | | 2521851 | 8/1983 |
| FR | | 2604080 | 9/1986 |
| FR | | 2627074 | 2/1988 |
| FR | | 2630365 | 4/1988 |
| FR | | 2690329 | 4/1992 |
| GB | | 2119941 A | 11/1983 |
| GB | | 2119941 | * 11/1983 |
| GB | | 2201801 A | 9/1988 |
| WO | WO 89/04139 | | 5/1989 |
| WO | WO 92/05736 | | 4/1992 |
| WO | WO 94/09446 | | 4/1994 |
| WO | WO 94/10900 | | 5/1994 |
| WO | WO 96/07978 | | 3/1996 |
| WO | WO 97/05578 | | 2/1997 |

OTHER PUBLICATIONS

Radke, Auf einem Blick, Funkschau, vol. 59, No. 1, Jan. 1987, Munchen.

Industrial Cryptography, IEE Review, May 1996 —sales brochure.

Daugman, "High Confidence Visual Recognition of Persons by a Test of Statistical Independence", IEEE Transactions of Pattern Analysis and Machine Intelligence, vol. 15, No. 11, Nov. 1993.

Collection of web–pages from Identification Technologies International, 1997.

Web–page describing Sensar Inc.'s "I risident" system, 1997.

Karla Harby, "A Discerning Eye", p. 29, Scientific American, Apr. 1996.

Anjana Ahuja, "A Peep into the Future of Iris ID", The Times, Apr. 14, 1996.

* cited by examiner

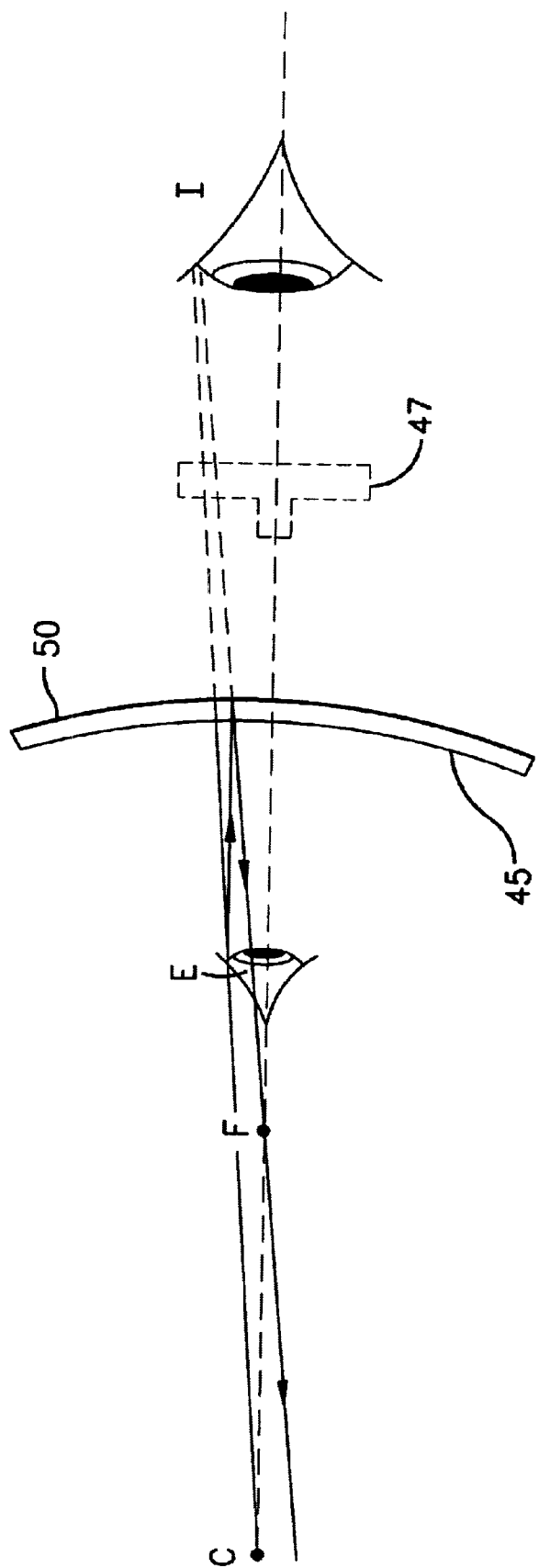

IMAGING APPARATUS

RELATED APPLICATIONS

This application is related to the following co-pending commonly assigned applications:

1. Seal et al, "Personal Identification", Ser. No. 09/194,319 filed Nov. 24, 1998.
2. Seal et al, "Personal Identification", Ser. No. 09/194,318 filed Nov. 24, 1998.
3. Seal et al, "Personal Identification", Ser. No. 09/194,737 filed Dec. 2, 1998.

BACKGROUND OF THE INVENTION

1. Field of the Invention

The present invention relates to an imaging apparatus. It has particular utility in relation to an imaging apparatus operable to obtain an image of one or more facial features of a user.

2. Related Art

One known apparatus of this type forms a component of the IriScan 2000 EAC™ iris recognition apparatus manufactured by IriScan Inc. The apparatus includes an image capture unit comprising a wall-mounted body portion which rotatably supports a tiltable housing containing the optical elements used in the apparatus. The camera and path-bending optics inside the housing are arranged so as to provide the camera with a view through an aperture provided in the front wall of the tiltable housing. The housing additionally contains a liquid crystal display (LCD display) which is viewed by the user during the iris recognition procedure through the same aperture. The LCD display is driven by the video signal which is currently being output by the camera.

In using the apparatus, the user moves his head until the LCD display shows an in-focus image of one of his eyes. Because of safety constraints on the level of illumination of the human eye, the depth of focus of the apparatus is limited and the user must position his head within a relatively narrow range of distances from the apparatus. The magnification of the optical system is arranged such that, when in focus, the image of one eye fills more than one-third of the field of view of the camera. This is useful in assuring that the iris is imaged in sufficient detail to obtain an iris data sequence which is unique to that iris.

The cost of the LCD display in the above apparatus is significant. Although the use of iris recognition technology is clearly desirable because of the high level of security it affords, the current cost of iris recognition units hinders their incorporation into credit card payment terminals and the like.

Other proposed iris recognition apparatuses avoid the requirement that the user moves his head to a preferred position in relation to the apparatus, instead providing a camera with both an auto-focus and an auto-zoom facility. Although this relaxes the constraints imposed on the distance between the user and the apparatus, it does not provide a facility for aligning the eye within the field of view of the camera. Hence, the use of a Pan Tilt Zoom camera in conjunction with eye-tracking techniques has been proposed to ensure that the user's eye is included within the obtained image. The use of such devices markedly increases the unit production cost of the imaging component of the iris recognition apparatus.

Identification Technologies International Inc. produce a PAC-1000 facial recognition system. The image capture part of the apparatus has a mirror on its front surface in which the user can see his reflection. Although this places constraints on the transverse position of the user's face, it does not place any positive constraints on the distance between the user and the device. The user is, of course, able to estimate his distance from the apparatus owing to its apparent size (i.e. owing to perspective), but that is not a sufficiently accurate indication to enable him reliably to adopt a preferred position in relation to the apparatus.

SUMMARY OF THE INVENTION

Accordingly, the present invention provides a facial feature imaging apparatus comprising:

a camera apparatus operable to capture an image of one or more facial features of a user, light reflected from said facial features travelling along an optical path from said facial features to said camera apparatus;

a visible light reflector disposed on said optical path, and positioned such that, in use, the user can see his reflection therein, said reflector being arranged to present a reflection of the user, which reflection gives a positive visual indication to the user that he is within a preferred range of distances from the camera.

By providing a visible light reflector which is arranged to present a positive visual indication to the user that he or she is within a preferred range of distances from the camera, feedback is provided to the user enabling him to position his head at a correct distance from the apparatus. The visible light reflector provides this feedback as effectively as known devices but more cheaply than has hitherto been possible. The provision of such a visible light reflector reduces the need for a camera with an auto-focus (and possibly auto-zoom) facility. Furthermore, by arranging the reflector to lie on optical path between the user and the camera, the apparatus is made more compact than known apparatuses. The reflection provides a positive indication in the sense that there is some indication other than the user being able to judge his distance from the camera owing to perspective.

Preferably, the reflector comprises one or more optical elements which, in combination, have an optical power greater than zero. This has the result that the reflection seen by the user undergoes changes in both size and orientation as the user approaches the apparatus.

Preferably, the reflector comprises a non-planar reflector, the surface of which is shaped so as to present said positive visual indication. The advantage of such visible light reflectors is that they comprise few components and hence are inexpensive to manufacture.

In preferred embodiments, the mirror presents a concave surface to the user. The concave surface may be spherical or aspherical. Spherical mirrors usually cost less than aspherical ones.

Some embodiments of the present invention use a camera which is responsive to light outside the visible portion of the electromagnetic spectrum. For example, the camera used may responsive to infra-red light, in which case the reflector used can be a wavelength-selective mirror, which reflects visible light but allows the passage of infra-red light, placed in the aperture in the housing. It will be appreciated that this arrangement allows infra-red light reflected from the user's face to pass through the mirror and continue along an optical path towards the camera.

BRIEF DESCRIPTION OF THE DRAWINGS

By way of example only, specific embodiments of the present invention will now be described with reference to the accompanying drawings in which:

FIG. 3A is an optical ray diagram illustrating the effect of the curved cold mirror on visible light;

DETAILED DESCRIPTION OF EXEMPLARY EMBODIMENTS

Figure 1:
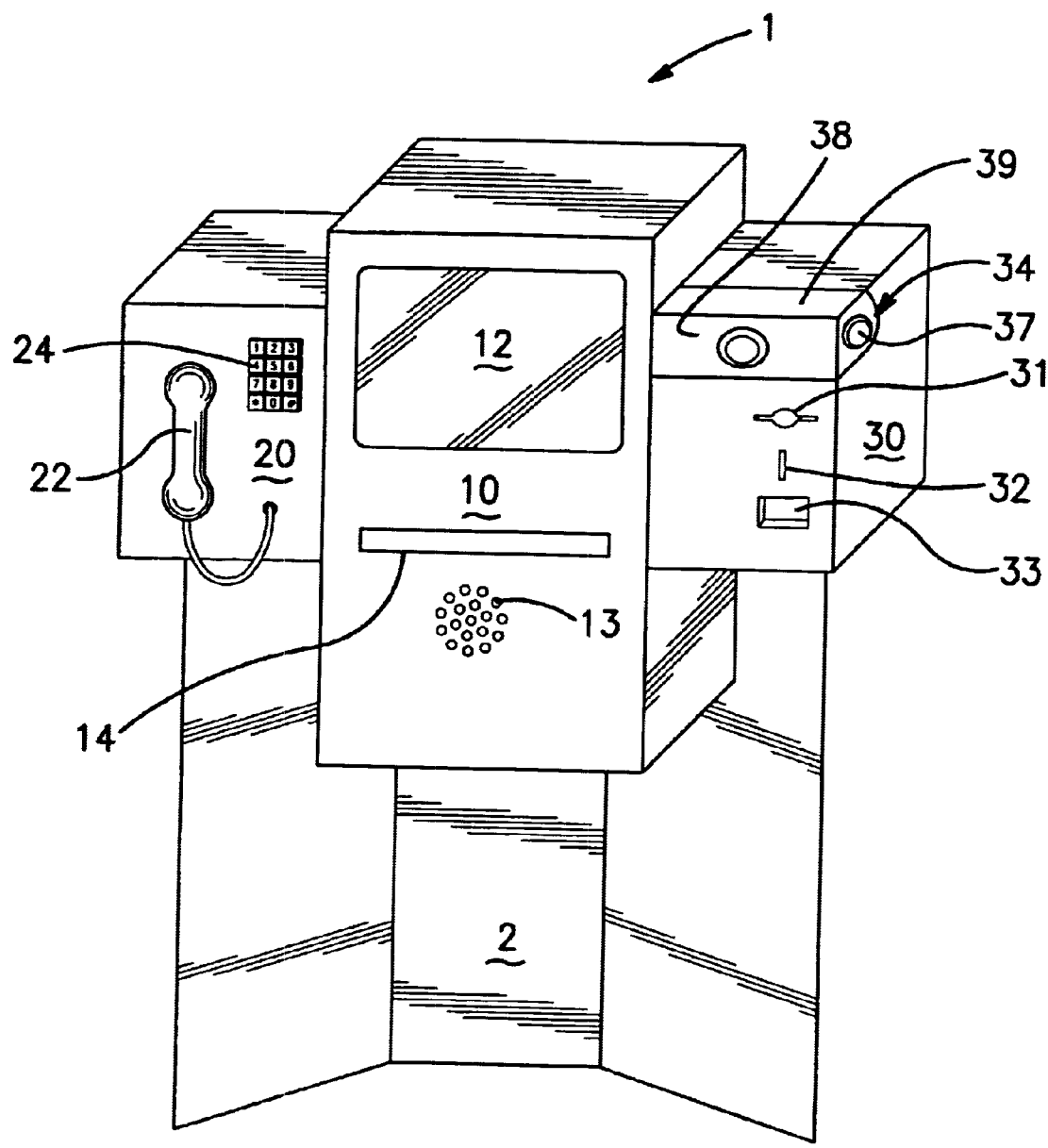
FIG. 1 shows a multimedia kiosk adapted to incorporate an iris data sequence generation unit.

FIG. 1 shows a multimedia kiosk 1 which is an adapted version of BT's Touchpoint® kiosk. The kiosk is connected via telecommunications links to remote servers and also to the Public Switched Telephone Network (PSTN). The kiosk comprises three sections 10,20,30 secured together and mounted on a supporting structure 2. The central user interface section 10 comprises a container housing a cathode ray tube (CRT) display 12, a printer and a loudspeaker 13. The CRT 12 displays information in the form of World Wide Web pages and also provides a touch screen facility allowing the user to interact with the kiosk. The kiosk provides printed output through a horizontal slot 14 in the front surface of the user interface section a few centimeters underneath the CRT screen. Audio output is provided via the loudspeaker 13.

The second component of the kiosk is a telephone section 20 secured to the left-hand side of user interface section 10 and which includes both a telephone handset 22 and a keypad 24 to enable the user to telephone from the kiosk.

The third component of the kiosk is a payment acceptance section 30 secured to the right-hand side of the user interface section 10. The payment acceptance section 30 has a credit-card slot 31, a coin slot 32 and a refund chamber 33. As so far described, the kiosk 1 is of conventional design.

However, the kiosk of the specific embodiment additionally has an iris recognition unit integrated into the upper part of the payment acceptance section 30. Furthermore, the payment acceptance section 30 is also angled approximately fifteen degrees inwardly so that the user can divert his attention from the CRT screen 12 to the iris recognition unit without having to move his head sideways.

The iris recognition unit comprises an elongate image capture part 34 rotatably mounted at the front upper corner of the payment acceptance part 30 and iris data sequence generating electronics located in the rear upper part of the payment acceptance section 30.

The image capture part 34 comprises an elongate housing having three elongate sides (only two of which 38,39 are visible in the drawing) and two ends. The housing is provided with a disc-shaped handle 37 at its right-hand end. The handle 37 is concentric with the axis of rotation of the part 34. One side 38 of the housing is rectangular and is forwardly directed in a normal orientation (as shown in the drawing). An adjacent side 39 is of a similar rectangular shape and, in the normal orientation of the part 34, extends horizontally rearwardly from the forward panel. The other wall of the housing is provided by a surface corresponding to the surface of a cylinder having an axis coincident with the axis of rotation of the image capture part 34. It will be realised that the cylindrical surface meets the sides 38,39 at an angle of greater than 90 degrees.

Figure 2:
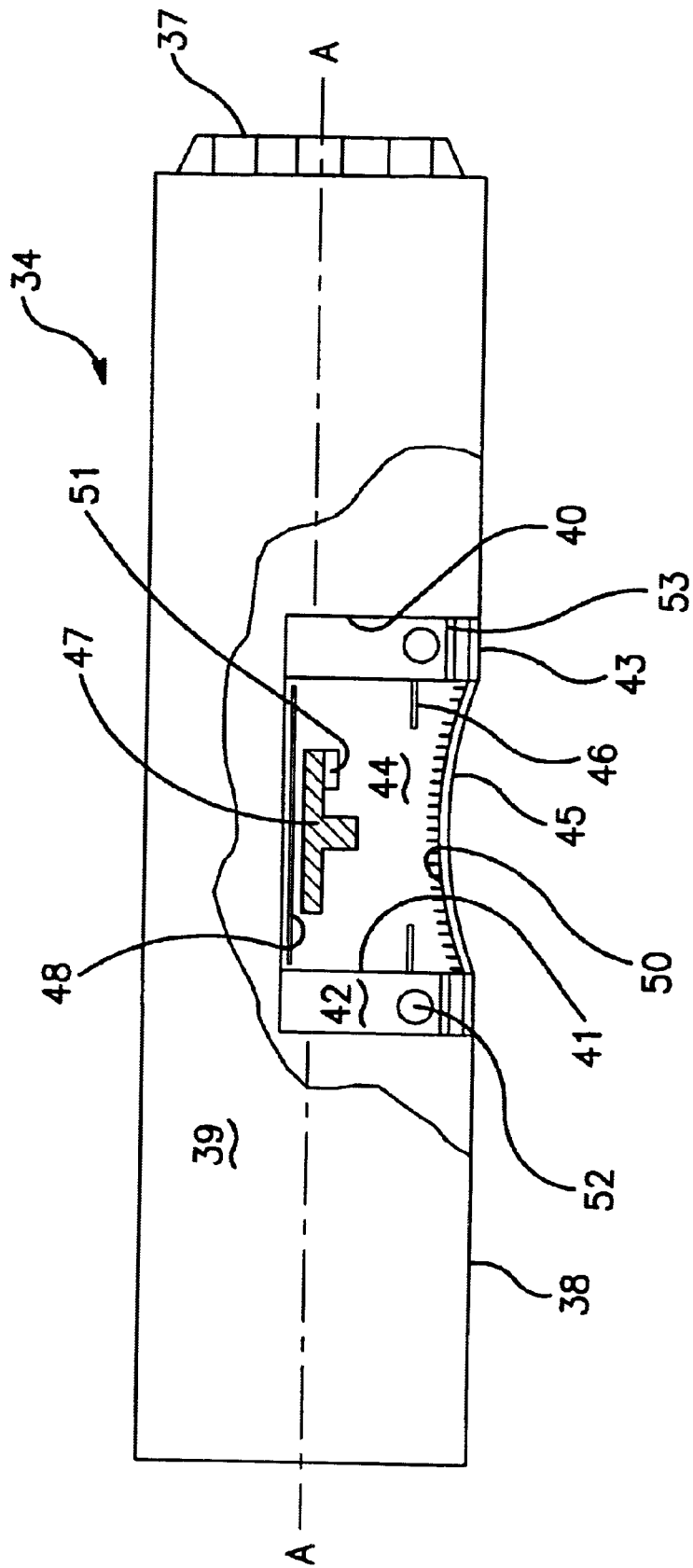
FIG. 2 is a schematic illustration, partly in cross-section, of the arrangement of components within an iris image capture part of the data sequence generation unit.

As can be seen from FIG. 2 (which shows the upper surface 39 partially cut away and the components below in cross-section) the forward side panel 38 has a centrally located cylindrical recess 40 which has a diameter of 80 mm and extends rearwardly from the edges of the aperture to a point approximately coincident with the axis of rotation AA of the part 34. Located concentrically inside the recess 40 is a cylindrical wall 41 of a height equal to the depth of the recess and enclosing a cylindrical chamber 44 having a diameter of 70 mm. The annular chamber 42 defined by the cylindrical wall 40 and the recess 41 is closed by a finely frosted glass ring 43. The open end of the cylindrical chamber 44 is closed by a curved mirror 45 which reflects visible light falling upon it. The cylindrical wall 41 is provided with a circumferential flange 46 located at a short distance behind the curved mirror 45.

A charged coupled device (CCD) camera 47 is centrally mounted on a circuit board 48 held at the bottom of the cylindrical recess 44. The camera 47 is a Watec Wat 660 imager unit and has dimensions of 30 mm*30 mm*18 mm. The camera 47 is combined with a 12 mm lens to provide a focused image of any object positioned about 100 mm in front of the camera. The camera 47 is responsive both to visible and infra-red light. Two light-emitting diodes (LEDs) (not shown) are mounted on the forward side of the circumferential flange 46, at its uppermost and lowermost points respectively. Connections to the LEDs run from the circuit board 48.

The curved mirror 45 is formed from a transparent glass substrate of 5 mm thickness and has the form of part of the surface of the sphere of radius 200 mm. A coating 50 is provided on the rear side of the glass substrate, the coating 50 being effective to reflect visible light (whose wavelength lies between around 400 nm and 700 nm) but to allow the transmittance of light of other wavelengths, including the infra-red light produced by the LEDs. Those skilled in the art of manufacturing such coatings will have little difficulty in making a coating having such properties.

The present inventors have established that the iris can be imaged most sharply in the very near infra-red (i.e. in a wavelength range from 700 nm to 850 nm). Longer wavelengths are thought to penetrate deeper into the eye and hence lead to an obscuration of the iris pattern. To alleviate this problem, the camera 47 is supplied with a filter (not shown) that substantially removes wavelengths greater than 850 nm.

Furthermore, owing to the effect of absorption by water and oxygen molecules in the atmosphere, there are several dips in the spectrum of natural sunlight in the 750 nm to 800 nm wavelength range. Imaging the iris in the 700 nm to 850 nm range therefore results the undesirable effect of reflections of infra-red light from the sun being reduced.

A range sensor 51 is mounted on the surface of the camera 47 and is operable to output a proximity signal when an object moves closer than 100 mm to the camera 47.

A fluorescent tube 52 formed into the shape of a ring save for its two ends which point rearwardly is positioned in the annular chamber 42. A ring shaped infra-red blocking filter 53 is located in the annular chamber 42 directly in front of the fluorescent tube 52. The two ends of the tube 52 are held in the base of the cylindrical recess 44 and are connected to sliding contacts (not shown) on the curved side of the image capture part 34.

The electronics associated with capturing a data sequence which characterises the user's eye are located outside the image capture part 34 of the iris recognition unit in the upper part of the payment acceptance section 30. One algorithm which may be executed by the electronics in order to characterise the iris of the user is described in U.S. Pat. No. 5,291,560. Electronic communication between the image capture unit and the data sequence generating electronics is provided by further sliding contacts on the cylindrical surface of the image capture part 34. Similar sliding contacts are used to allow power to be transmitted to the fluorescent tube 52, camera 47 and LEDs.

In using the modified Touchpoint® kiosk, interaction between the user and the kiosk may, for example, be as follows. Initially, the user steps up to the kiosk and views the main menu displayed on the CRT screen 12. He will normally adopt a position around 500 mm from the screen 12 and payment acceptance unit 30 to do this. The user then uses the touch screen facility to (for example) order some merchandise to be delivered to his home. If he chooses to pay by credit card at this stage then the display prompts him to enter his credit card into the credit card slot 31 on the payment unit 30, the payment unit 30 then reading account details from the card in a conventional manner. At this time, the fluorescent tube 52 is illuminated and a message on the screen 12 (or perhaps a voice prompt from loudspeaker 13) prompts the user to move his eye forwardly until the point where he sees an upright focused image of his eye in the mirror 45. Initially, the user must manipulate the handle 37 to tilt the mirror such that he can see an image which includes his eye. Thereafter, as explained below, in order to see an upright image of his eye in the mirror, the user must move to within 100 mm of the image capture part 34. Once the user has moved that close to the image capture part 34, the range sensor 51 outputs the proximity signal mentioned above. On generation of the proximity signal, the camera 47 begins to capture images of the user, the LEDs 52 being lit in synchrony with the moments of image capture. Further images are captured until one suitable for forming an iris representing data sequence is obtained. Once the image has been successfully captured, a voice message is output indicating that the image has been captured and thanking the user for having presented his eye. The iris representing data sequence is then transmitted to a remote server where a check can be made to see whether the iris data sequence matches that of the person to whom the card was issued. If such a match exists, then a signal is sent back to the kiosk to indicate that the transaction may be allowed.

Figure 3B:
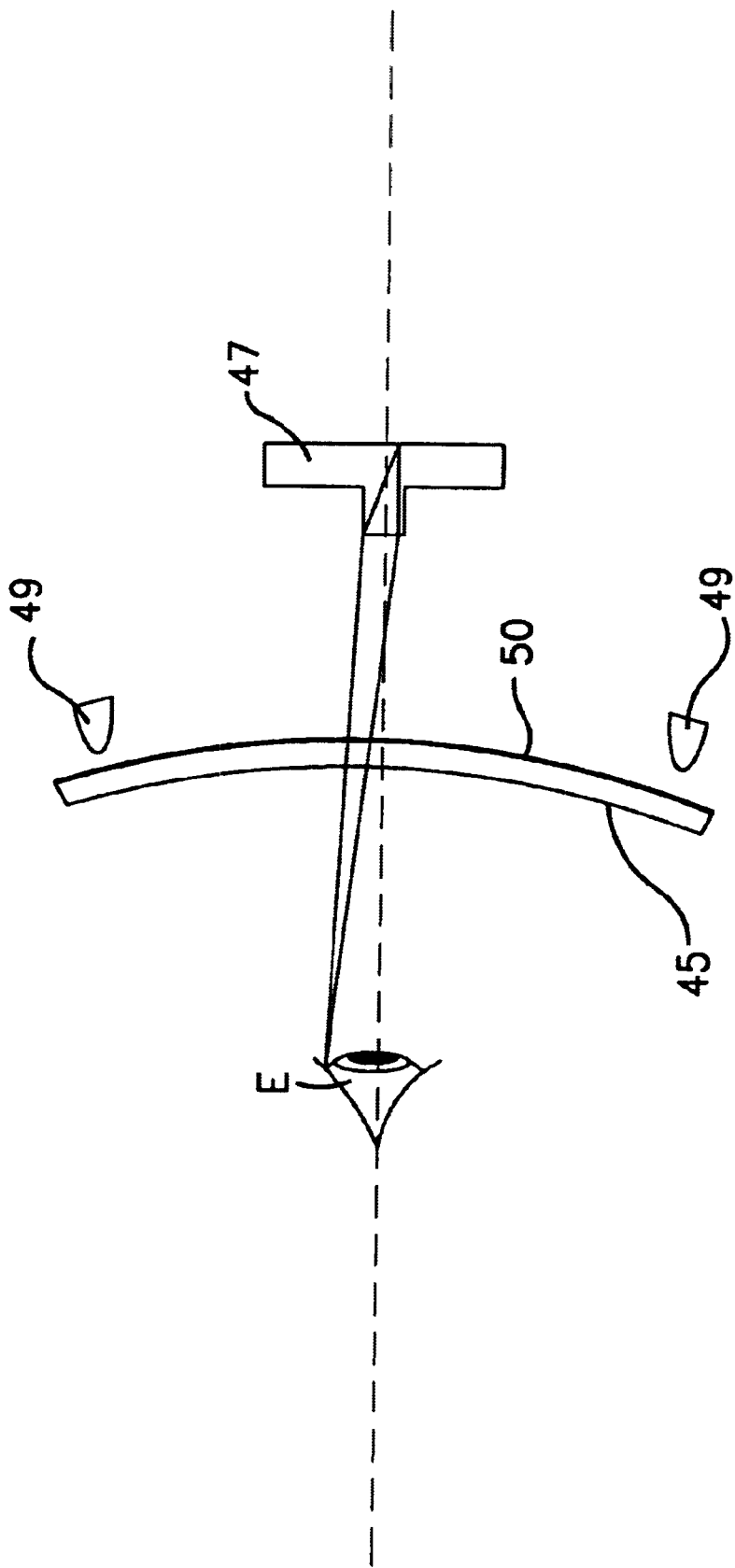
FIG. 3B is an optical ray diagram illustrating the passage of infra-red light reflected from the user's eye.

The function of each of the optical elements used in the image capture part will now be explained in relation to FIGS. 3a and 3b. FIG. 3a illustrates the interaction of the optical elements with visible light. On the user inserting his credit card into the payment unit 30, visible light from his external surroundings and also from the fluorescent tube 52 falls upon his eye (E) and is reflected toward the cold mirror 45. It is likely that the user will initially be around 500 mm from the mirror 45, and the reflection he sees will therefore be an inverted image of his surroundings. Following the instruction from the kiosk for him to move inwards towards the mirror 45 until he sees an upright image of his eye, the user will move towards the mirror 45 and will see the inverted image increase in size until it becomes an unrecognisable blur. However, as the user moves inwardly from a distance (F) 100 mm from the cold mirror 45, the image (I) will begin to reduce in size and will appear the right way up. At this Point the user will stop moving forwards. Since the user is then less than 100 mm from the mirror 45, the range sensor 51 will start to output the proximity signal.

The position at which the user considers the reflection of his eye to be in focus will depend on whether he is short or long-sighted. Since the position of the upright virtual image seen by the user is initially very far away and then comes closer as he moves forward, the use of a curved mirror means that even long-sighted people (who might not be able to see an upright focused image at all if a plane mirror were to be used) will find a distance at which their reflection appears focused.

Since the cold mirror 45 is largely ineffective in the very near infra-red, the infra-red optical behaviour is relatively simple and is illustrated in FIG. 3b. On the two LEDs lighting, the infra-red light will pass from the LEDs through the cold mirror 45 and will thereafter be reflected off the user's eye (E) towards the camera 47. Since the user is at a distance of less than 100 mm from the mirror 45, the image of the user's iris should fill a reasonable proportion of the image captured by the camera 47.

In this position, most of the visible light falling upon the user's eye (E) will have emanated from the fluorescent tube 52. The image captured by the camera 47 may be spoiled if a reflection of a diffuse infra-red light source is seen by the camera to wash out some of the detail of the user's iris. The function of the infra-red blocking filter 53 is to reduce the already small component of infra-red light output by the fluorescent tube 52 further so as to avoid such washing out of the image.

The above has assumed that the cold mirror 45 has no effect on infra-red light. However, in practice, a small percentage of the infra-red light may be reflected by the coating 50. The curved mirror 45 presents a convex surface to the camera 47 and it is an advantage of the use of a curved mirror 45 that light from the LEDs undesirably reflected from the coating is generally reflected outwardly away from the camera 47.

In a second embodiment of the present invention, additional guide markings are painted on the front surface of the curved mirror 45. The guide markings comprise the central sections of the sides of a horizontally oriented 30 mm*20 mm rectangle centred at the centre of the mirror 45.

The use and operation of the apparatus are as described in relation to the first embodiment save for the following points. In addition to the prompt issued by the kiosk requesting the user to move forward until he sees a right way up reflection (I) of his eye, the user is further prompted to move to a distance such that the outer boundaries of the reflection of his eye (I) correspond as closely as possible to the guide markings. Not only does this encourage the user to align his eye centrally in the field of view of the camera, since the size of the reflection (I) of the user's eye varies with distance from the mirror 45, it further results in the user being guided to a more tightly defined preferred distance from the camera 47.

Figure 4A:
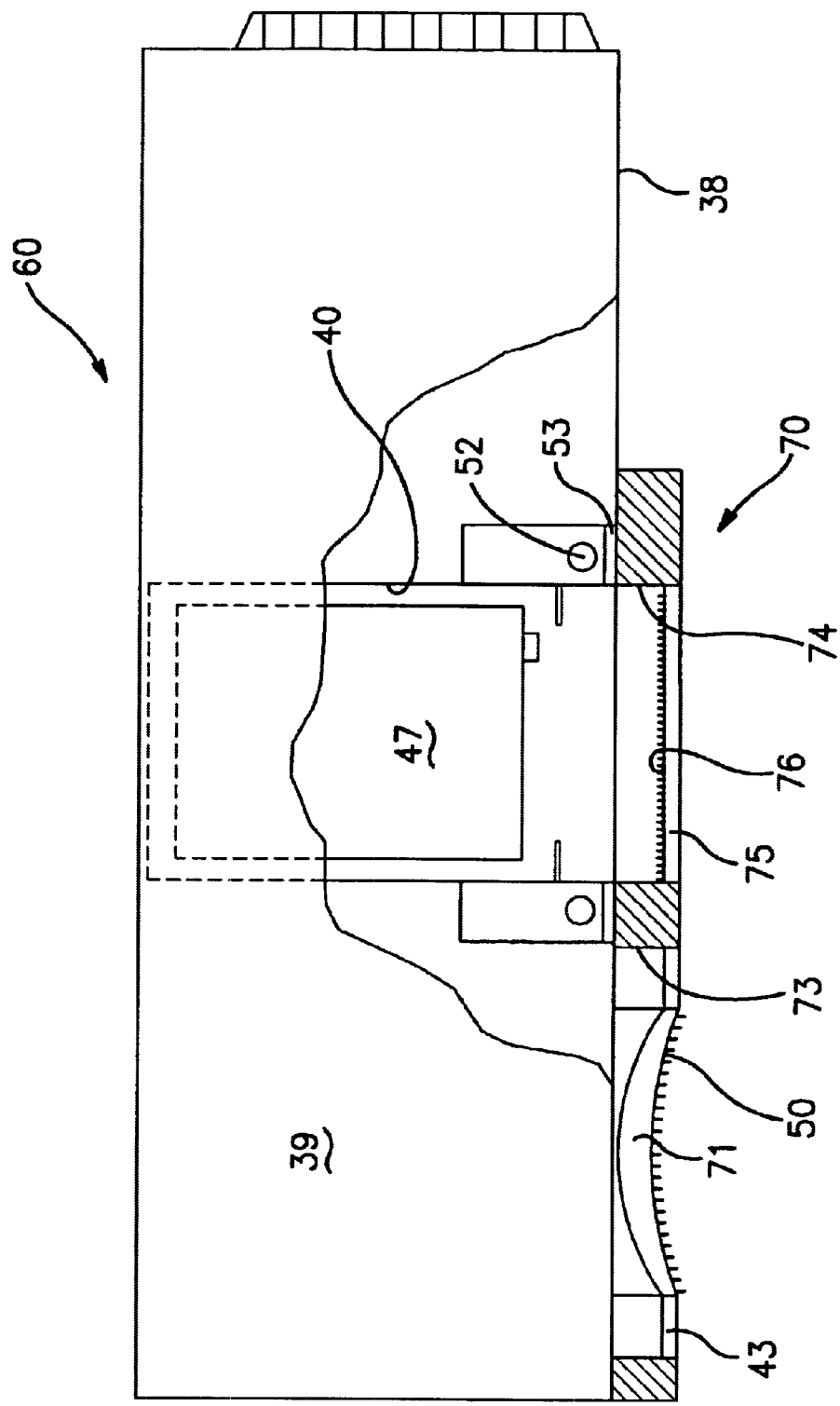
FIG. 4A is a schematic illustration, partly in cross-section, of the arrangement of components within an iris image capture part of a third embodiment of the present invention in a normal configuration suitable for video-conferencing.
Figure 4B:
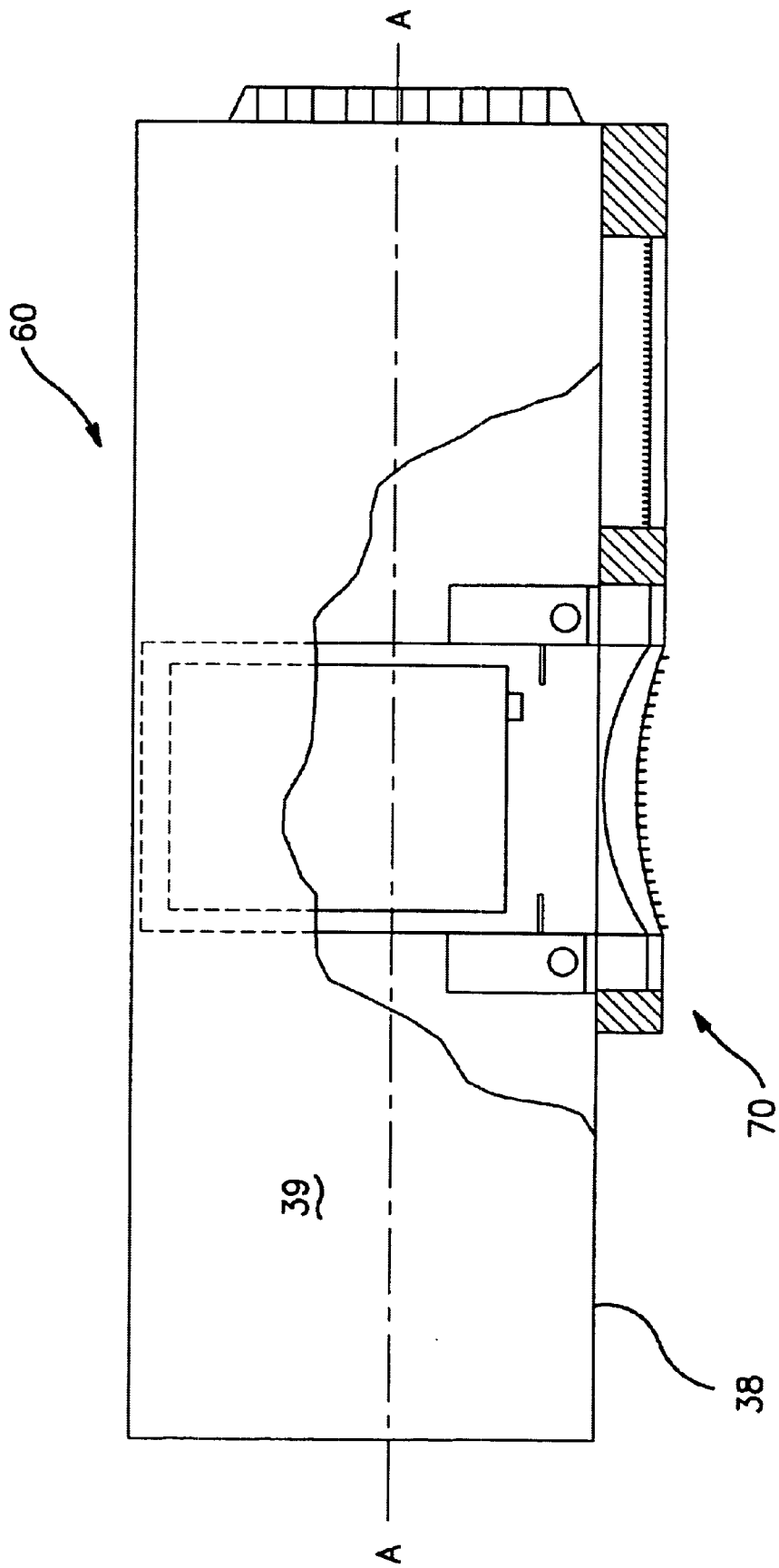
FIG. 4B shows the image capture part of FIG. 4A in a configuration suitable for capturing an image of the user's iris.

A third embodiment of the present invention is illustrated in FIGS. 4A and 4B.

Some multimedia kiosks provide a video-conferencing facility so that the user may have a video-conference with, for example, a sales assistant at the store from which he wishes to buy something. In this case, using only a single camera for both the video-conferencing and the iris recognition enables both the design and the use of the apparatus to be simplified.

The problem that then faces the designer is that video-conferencing cameras often cannot provide an image of an object close to the camera, which image is both focused and magnified to the degree required for iris recognition.

The third embodiment (FIGS. 4A and 4B) implements one solution to this problem. The embodiment shares any of the features of the first embodiment illustrated in FIGS. 1 and 2 and features common to both embodiments are given like reference numerals and not described further here. In the embodiment, a Touchpoint® multimedia kiosk is modified by the addition of an iris image capture part and is data sequence generating electronics. In contrast to the first embodiment, the iris imaging unit is located on the front upper edge of the central user interface section and is also used to obtain pictures of the user for use in a video-conference with another party. The iris data sequence generating electronics are housed in the central section behind the image capture part.

The iris imaging unit comprises a main body 60 and a slider 70. The main body is substantially identical to the image capture part described in relation to the first embodiment, save for the following. Firstly, the forward and upper sides 38,39 have transverse dimensions which are large enough to accommodate a 120 mm deep cylindrical recess 40 in the centre of the front side 38. The recess 40 holds a Sony EVI 331 colour camera block 47 which has dimensions of approximately 50 mm*50 mm*100 mm. The camera has had the infra-red blocking filter which it normally contains removed. A second difference in the image capture unit is that the curved mirror and the frosted glass ring have been removed. The infra-red blocking filter 53 in front of the fluorescent tube 52 replaces the finely frosted glass ring and closes the annular chamber 42.

The slider 70 comprises a rectangular panel which has a depth of 15 mm, a height similar to that of the forward side 38 and a length 100 mm less than the forward panel 38. The slider is aligned with the forward panel 38 and is slidably mounted thereon. The slider is movable horizontally from a leftmost position (FIG. 4A) where its left-hand edge is flush with the left-hand edge of the main body 60 to a rightmost position (FIG. 4B) where the right-hand edge is flush with the right-hand edge of the main body 60.

The slider 70 has two circular apertures 73,74. The left-hand aperture has a diameter of 80 mm which holds an annular frosted glass ring 43 identical to that used in the first embodiment. A wall 72 extends 10 mm rearwardly from the inner edge of the glass ring 43. A close-up lens 71 of 70 mm diameter is held in the aperture defined by the inner edge of the wall 72. The front surface of the close-up lens is of identical shape to the rear surface of the curved mirror 45 and is provided with a similar coating 50. The lens 71 is shaped to have a power of around 4 dioptres—those skilled in the art of lensmaking will have little difficulty in producing such a lens.

The right-hand aperture holds a plane glass disc 75 of 70 mm diameter. The rearward side of the disc is coated with an infra-red blocking coating 76.

A solenoid and controlling electronics are provided and are operable to move the slider 70 between its leftmost and rightmost positions.

In use, the slider 70 is initially in its leftmost position, and the user may order goods in the same way as described in relation to the first embodiment except that he is now additionally involved in a video-conference with a sales assistant at the store from which he wishes to buy goods. If the user elects to pay using his credit card, then on inserting his card, the slider 70 is driven to its rightmost position and the fluorescent tube 52 is lit. The user is then asked to move forward until he can see an upright image of his eye in the mirrored surface of the close-up lens 71. Once a suitable image of his iris has been captured, he is thanked for having presented his eye and the solenoid drives the slider 70 back to its leftmost position.

The role of the optical elements in the third embodiment will now be explained. When the slider 70 is in its leftmost position (FIG. 4A), the camera 47 views the user through the plane glass disc 75. The disc 75 has no optical power and does not affect the range of distances over which the camera can focus. However, the coating 76 on the disc 75 substitutes for the infra-red blocking filter which has been removed from the camera 47. Hence the camera can operate normally as a colour video-conferencing camera when the slider 70 is in the leftmost position.

However, when the slider 70 is in its rightmost position (FIG. 4B), the coating 50 on the outer surface of the close-up lens 71 prevents visible light from reaching the camera 47. The surfaces of the lens 71 are effective to refract infra-red light produced from the LEDs and reflected from the user's eye. The lens has positive power and hence, given the required magnification (an eye positioned 100 mm from the camera should fill at least one third of the field of view of the camera) lowers the lower limit of the range of distances over which the camera 47 can provide a focused image suitable for iris recognition purposes. In practice, the object distance at which the Sony EVI 331 colour camera block could provide such an image was reduced from 300 mm to 60 mm by the addition of such a lens.

Although the above embodiments have used a cold-mirror, it will be realised by those skilled in the art that the camera could be responsive to visible light and a partially reflecting mirror could be used. The infra-red LEDs could be replaced with white light LEDs (now manufactured by Nichia of Japan) and a portion of the light from them reflected on the user's face would fall on the mirror and be reflected thereby enabling the user to position himself correctly. The remainder of the visible light could provide the required image of the user's iris.

In some embodiments, the visible light reflector could be formed of a combination of optical elements. For example, the curved mirror described above could be replaced by a combination of a suitably selected lens and a planar mirror.

Both the above embodiments feature a spherical mirror 45 which presents a concave surface towards the user. However, it is possible, for example, to use an aspherical mirror which is designed to distort the user's reflection if the user is incorrectly transversely aligned.

In other implementations, the mirror might be located at a distance from the aperture, even when in use. For example, the mirror might be placed inside the housing behind the aperture.

The 200 mm radius of curvature of the reflecting surface used in the above embodiments was chosen because it results in the user being constrained to adopt a position within a narrow range of distances from the camera. In principle, however, the curvature of the mirror could be relaxed to, for example, radiuses of curvature as great as 1 m. It is probable however that an auto-focus camera would then be needed. Although obtaining a suitably magnified focused image would then be possible without the use of a close-up lens, problems owing to camera shake or user movement might then become apparent.

The above embodiments describe the use of a concave mirror. However, a convex mirror might also be used. In such embodiments, the user would perceive the size of his reflection to increase in relation to the size of the mirror as he advanced towards the mirror. Then mirror could be marked so that the user's reflection became aligned with the markings on the user reaching a preferred working distance from the apparatus. An advantage of using a concave mirror is that it cannot focus light onto the user's eye. There will therefore be fewer safety related design constraints in embodiments using a concave mirror.

The above embodiments have related to a kiosk having an integral iris recognition unit. However, a curved mirror might also be placed in the entrance window of the hand-held imager described in International Patent Applications WO 97/46978, WO 97/46979, and WO 97/46980. The curved mirror would then have a diameter of only around 2 cm and would have a radius of curvature so as to create a focal point around 5 cm from the mirror. In this way a hand-held imager is created that advantageously does not require the user to bring the imager right up to his eye.

It will be seen how the embodiments of the present invention provide an inexpensive facility allowing a user to adopt a preferred position in relation to an imaging apparatus.

What is claimed is:

1. A facial feature imaging apparatus comprising:

a camera apparatus operable to capture an image of one or more facial features of a user, light reflected from said facial features traveling along an optical path from said facial features to image capturing means within said camera apparatus;

a visible light reflector disposed, in use, across said optical path, and such that the user can see his reflection therein, which reflection gives a positive visual indication to the user that he is within a preferred range of distances from the camera for capturing said image;

wherein said reflector comprises a non-planar reflector, the surface of which is shaped so as to present said positive visual identification.

2. An apparatus according to claim 1 wherein said reflector comprises one or more optical elements which, in combination, have an optical power greater than zero.

3. An apparatus according to claim 2 wherein said reflector comprises a mirror.

4. An apparatus according to claim 2 wherein said reflector comprises a lens having a reflective coating thereon.

5. An apparatus according to claim 1 wherein said visible light reflector comprises a curved reflector whose concave surface is viewed by the user.

6. An apparatus according to claim 1 wherein the positive optical indication is the uprightness of the reflection.

7. An apparatus according to claim 1 wherein said reflector is provided with markings to be aligned with one or more of the user's facial features.

8. An apparatus according to claim 1 wherein said camera is responsive to non-visible light and said reflector allows the passage of said non-visible light.

9. An apparatus according to claim 1 wherein said apparatus is for capturing an image or images of an iris.

10. An identification apparatus comprising a facial feature imaging apparatus according to claim 1, a storage means storing one or more facial feature data sequences and a comparison means for comparing facial feature data sequences derived from one or more images obtained by the imaging apparatus with the one or more facial feature data sequences stored in the storage means.

* * * * *